United States Patent [19]

Synek

[11] Patent Number: 4,892,577
[45] Date of Patent: Jan. 9, 1990

[54] SOLUTION OF 3-ALKYLTHIO-4-AMINO-6-TERT.-BUTYL-1,2,4-TRIAZIN-5-ONES IN NORMALLY LIQUID N-ARYL-N-ALKOXYALKYL-HALOACETAMIDES

[75] Inventor: Joseph Synek, Overland Park, Kans.

[73] Assignee: Mobay Corporation, Pittsburgh, Pa.

[21] Appl. No.: 801,885

[22] Filed: Nov. 26, 1985

[51] Int. Cl.$^4$ .............................................. A71N 43/4
[52] U.S. Cl. .......................................... 71/93; 71/118; 71/DIG. 2
[58] Field of Search ............................................ 71/93

[56] References Cited

U.S. PATENT DOCUMENTS 3,986,862 10/1976 Armstrong ................................ 71/93
4,150,968 4/1979 Young et al. ............................ 71/93

OTHER PUBLICATIONS

Farm Pesticide Dictionary, (1985), p. C155.

*Primary Examiner*—Catherine L. Mills
*Attorney, Agent, or Firm*—Joseph C. Gil; Lyndanne M. Whalen

[57] ABSTRACT

In the preparation of an aqueous herbicidal composition containing a 3-alkylthio-4-amino-5-tert.-butyl 1,2,4-triazin-5-one and a N-aryl-N-alkoxyalkyl haloacetamide, the improvement which comprises dissolving the triazinone in at least twice its weight of the haloacetamide, and adding such solution to water. Advantageously an emulsifier is present and, if desired, prior to addition to water the solution is diluted with a solvent selected from the group consisting of a normally liquid optionally halogenated and/or alkylated aromatic hydrocarbon. This permits simplified preparation by the farmer of the aqueous dispersion he will apply to crops and fields.

17 Claims, No Drawings

SOLUTION OF 3-ALKYLTHIO-4-AMINO-6-TERT.-BUTYL-1,2,4-TRIAZIN-5-ONES IN NORMALLY LIQUID N-ARYL-N-ALKOXYALKYL-HALOACETAMIDES

The invention relates to improvements in making up suspensions containing the known herbicides 3-alkylthio-4-amino-6-tert.-butyl-1,2,4-triazin-5-one and a normally liquid N-aryl-N-alkoxyalkyl-haloacetamide.

3-Methylthio- and 3-ethylthio-4-amino-6-tert.-butyl-1,2,4-triazin-5-one are known as highly selective herbicides in cultivation of crops such as soy beans, wheat, and the like as described in U.S. Pat. No. 3,671,523.

N-aryl-N-alkoxyalkyl-haloacetamide, such as N-(2-ethyl-6-methylphenyl)-N-(2-methoxy-1-methylethyl)-chloroacetamide (Dual), are also known selective herbicides.

In certain instances where there are a great many different weeds to be combatted, each of the foregoing categories is not alone sufficient to kill all the weeds so it has been proposed to use the two categories in conjunction (1985 Farm Pesticide Dictionary, page C 155).

While not disclosed in the published literature, it is believed the way the two categories were used in conjunction was to mix into water metered amounts of the individual ingredients with surface active agents, both ingredients being water insoluble. The acetamide is normally liquid and could therefore be metered in relatively easily. The triazinone is normally solid and poses more of a problem in metering in, also requiring much mixing to achieve uniform suspension.

Accordingly, it is common first to form a concentrated liquid formulation containing the triazinone and surface active agent and to meter this formulation into the water. The formulation has been an aqueous suspension containing 40% of triazinone and conventional emulsifiers.

This works quite satisfactorily but it requires first formulating the triazinone, then selling the farmer two liquids, each containing emulsifiers, and his having to meter two substances into the water in the tank he will use for a herbicide spray.

In U.S. Pat. No. 4,150,968 there is described a herbicidal mixture of metribuzin and alachlor, N-(2,6-diethylphenyl)-N-methoxymethyl-chloroacetamide. Both substances are normally solid and are mixed with much solvent and emulsifier, then heated, to form a solution which can thereafter be applied directly or after being emulsified in water.

It is accordingly an object of the present invention to provide a simplified way of obtaining an aqueous suspension of the aforementioned triazinone(s) and certain acetamides, suitable for application to crops and fields in which said crops are growing or are to be grown.

These and other objects and advantages are realized in accordance with the present invention pursuant to which it has been found that the triazinone will dissolve in at least twice its weight of the haloacetamide, preferably at least four times its weight, when such haloacetamides are liquid. The resulting solution is stable and will not precipitate out either ingredient even upon cooling to the coldest temperatures anticipated during application of the herbicides. Surprisingly, its viscosity is almost that of the haloacetamide alone, beneficial in colder climates.

For dispersal in water, the volumes of active material are quite small and better results are achieved by using active materials diluted with organic solvents. In accordance with another aspect of the invention it has been found that the solutions of the triazinone in the haloacetamide are fully miscible with optionally halogenated and/or alkylated aromatic hydrocarbons such as benzene and naphthalene, e.g. toluene and xylene. Thus three component solutions can readily be made and then the farmer need meter into his water-containing tank only a single liquid.

The solutions containing solvent, triazinone and haloacetamide advantageously also contain emulsifiers and surface active agents of known kind and amount to facilitate forming the aqueous dispersion. Anionic, cationic and/or non-ionic agents, e.g. alkylaryl-sulphonates, ethoxylated phenols, and the like, such as Atlox 3409, T-Mulz 94 W and Sponto A1 69-40, have proven effective. Such agents are desirably present in about 4 to 10%, and preferably about 8%, by weight of the total active ingredients. The haloacetamides are normally liquid and advantageously of the formula

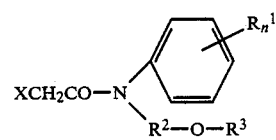

in which
X is halo, preferably chloro,
$R^1$ is hydrogen, halo or lower alkyl, preferably methyl or ethyl,
n is 0, 1 or 2, preferably 2,
$R^2$ is lower alkylene, preferably $C_2H_4$ or $CH(CH_3)—CH_2—$, and
$R^3$ is lower alkyl, preferably methyl or ethyl. The single most preferred acetamide is of the formula

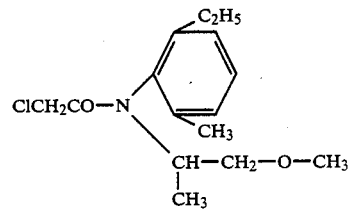

The invention will be further described in the following examples wherein all parts are by weight unless otherwise expressed.

EXAMPLE 1

Technical grade 4-amino-3-methylthio-6-tert.-butyl-1,2,4-triazin-5-one (92.8% active ingredient) was dissolved in different amounts of technical grade N-(2-ethyl-6-methylphenyl)-N-(2-methoxy-1-methylethyl)-chloroacetamide (96.7% active ingredient) and the following results were obtained:

| Weight Ratio Acetamide:Metribuzin | Crystallization At 32° F. |
| --- | --- |
| 19 | None after 2 months |
| 9 | " |
| 5.7 | " |
| 4 | " |
| 2.3 | After 4 weeks |
| 1.5 | After 4 weeks |

| Weight Ratio Acetamide:Metribuzin | Crystallization At 32° F. |
|---|---|
| 1 | Promptly, at room temperature |

To obtain the solutions with less than about 4:1 weight ratios low heat was used to accelerate dissolution, not necessary with the others.

Each of the foregoing solutions was infinitely miscible with toluene and xylene.

EXAMPLE 2

Solutions were made up as in Example 1 except that the metribuzin was replaced by its 3-ethylthio homologue. The following results were obtained after 3 days at 32° F.:

| Weight Ratio | Crystallization |
|---|---|
| 19 | None |
| 9 | " |
| 5.7 | " |
| 4 | " |
| 2.3 | Slight |
| 1.5 | Promptly, at room temperature |

EXAMPLE 3 (Comparison)

(a) A 1:19 solution of N$^1$-(3,4-dichloro-phenyl)-N,N-dimethylurea (Diuron) in the haloacetamide of Example 1 was prepared and it did not crystallize after 3 days at 32° F. but 1:9 and 1:57 solutions crystallized promptly even at room temperature.

(b) A 1:19 solution of 2-chloro-4-ethylamino-6-isopropylamino-s-triazine (Atrazine) in the haloacetamide of Example 1 turned cloudy after 3 days at 32° F.; at 1:9 solution had crystallized after 3 days at room temperature.

(c) A 1:19 mixture of 2-chloro-4,6-bis-ethylamino-s-triazine (Simazine) and the haloacetamide of Example 1 did not form a solution even upon heating at 120° C. Upon separating the solids and cooling the remaining solution at room temperature, material crystallized out.

This example shows that other herbicides do not form comparably stable solutions in the acetamides of the present invention.

EXAMPLE 4

A solution was prepared from the following ingredients:

| | Parts by Weight |
|---|---|
| Metribuzin | 1580 |
| Dual | 6900 |
| Xylene | 260 |
| Sponto AL 69-40 (emulsifier) | 630 |

The resulting solution was infinitely miscible with toluene and xylene and could be rapidly dispersed into water by stirring. The aqueous dispersion could be used in conventional manner for application to crops and fields.

Thus it is possible to obtain solutions highly concentrated with respect to active ingredient, i.e. containing little inert solvent, and yet the solutions can readily form suspensions in water.

It is understood that the specification and examples are illustrative but not limitative of the present invention and that other embodiments within the spirit and scope of the invention will suggest themselves to those skilled in the art.

I claim:

1. A solution of a 3-alkylthio-4-amino-6-tert.-butyl-1,2,4-triazin-5-one in at least twice its weight of a normally liquid N-aryl-N-alkoxyalkyl-haloacetamide.

2. A solution according to claim 1, containing the acetamide in about four to six times the weight of the triazinone.

3. A solution according to claim 1, diluted with a solvent selected from the group consisting of a normally liquid optionally halogenated and/or alkylated aromatic hydrocarbon.

4. A solution according to claim 1, diluted with a solvent selected from the group consisting of benzene and naphthalene optionally halogenated and/or alkylated.

5. A solution according to claim 2, diluted with toluene or xylene.

6. A solution according to claim 5, wherein the 3-alkylthio- is 3-methylthio.

7. A solution according to claim 5, wherein the 3-alkylthio is 3-1 ethylthio.

8. A solution according to claim 1, wherein the haloacetamide is of the formula

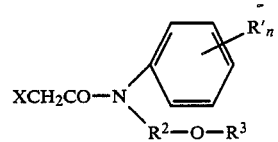

in which
X is halo,
R$^1$ is hydrogen or lower alkyl,
n is 0, 1 or 2,
R$^2$ is C$_2$H$_4$ or CH(CH$_3$)—CH$_2$, and
R$^3$ is lower alkyl.

9. A solution according to claim 8, in which
X is chloro,
R$^1$ is methyl or ethyl, and
R$^3$ is methyl or ethyl.

10. A solution according to claim 1, wherein the haloacetamide is N-(2-ethyl-6-methylphenyl)-N-(2-methoxy-1-methylethyl)-chloroacetamide.

11. A solution according to claim 1, containing about 4 to 10% of an emulsifier based on the weight of triazinone and haloacetamide.

12. A solution according to claim 1, wherein the 3-alkylthio- is 3-methylthio, the haloacetamide is N-(2-ethyl-6-methylphenyl)-N-(2-methoxy-1-methylethyl)-chloroacetamide and it is present in about 4 to 6 times the weight of the triazinone.

13. A solution according to claim 12, diluted with toluene or xylene.

14. In the preparation of an aqueous herbicidal composition containing a 3-alkylthio-4-amino-6-tert.-butyl-1,2,4-triazin-5-one and a N-aryl-N-alkoxyalkyl haloacetamide, the improvement which comprises forming a solution containing the triazinone in at least twice its weight of the haloacetamide plus an emulsifier, and adding such solution to water.

15. A process according to claim 14, wherein prior to addition to water the solution is diluted with a solvent selected from the group consisting of a normally liquid optionally halogenated and/or alkylated aromatic hydrocarbon.

16. A process according to claim 14, wherein the triazinone is dissolved in about four to six times its weight of the haloacetamide.

17. A solution according to claim 1, comprising approximately by weight 1580 parts of metribuzin, 6900 parts of N-(2-ethyl6-methylphenyl)-N-(2-methoxy-1-methylethyl)-chloroacetamide, 260 parts of xylene and 630 parts of an emulsifier.

* * * * *